US008992832B2

(12) United States Patent
Donnerbauer et al.

(10) Patent No.: US 8,992,832 B2
(45) Date of Patent: Mar. 31, 2015

(54) LUMINESCENCE METHOD OF DETECTING AN ANALYTE IN A LIQUID SAMPLE AND ANALYSIS SYSTEM

(71) Applicant: Roche Diagnostics Operations, Inc., Indianapolis, IN (US)

(72) Inventors: Erna Donnerbauer, Eberfing (DE); Ursula Giesen, Weilheim (DE)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 0 days.

(21) Appl. No.: 13/749,900

(22) Filed: Jan. 25, 2013

(65) Prior Publication Data

US 2013/0189798 A1     Jul. 25, 2013

(30) Foreign Application Priority Data

Jan. 25, 2012   (EP) .................................... 12152363

(51) Int. Cl.
  *G01N 21/76*   (2006.01)
  *G01N 21/64*   (2006.01)
  *G01N 33/543*   (2006.01)

(52) U.S. Cl.
  CPC ............ *G01N 21/76* (2013.01); *G01N 21/6408* (2013.01); *G01N 21/6428* (2013.01); *G01N 33/54326* (2013.01)
  USPC ....... 422/52; 422/82.08; 436/172; 435/288.7; 250/483.1; 702/19

(58) Field of Classification Search
  None
  See application file for complete search history.

(56) References Cited

U.S. PATENT DOCUMENTS

| 5,238,808 | A  |   | 8/1993  | Bard et al. |
| 6,599,473 | B1 |   | 7/2003  | Egger et al. |
| 6,881,536 | B1 |   | 4/2005  | Shah et al. |
| 2005/0142033 | A1 | * | 6/2005 | Glezer et al. ..................... 422/58 |
| 2007/0034529 | A1 | * | 2/2007 | Bard et al. ..................... 205/775 |
| 2009/0184259 | A1 |   | 7/2009 | Ma et al. |
| 2011/0293154 | A1 | * | 12/2011 | Meixner et al. ............... 382/128 |

FOREIGN PATENT DOCUMENTS

| WO |         86/02734 A1 |   | 5/1986 |
| WO |      2005/040759 A3 |   | 5/2005 |
| WO |       WO2010081690 | * | 7/2010 |

* cited by examiner

*Primary Examiner* — Melanie Y Brown
*Assistant Examiner* — Rebecca Martinez
(74) *Attorney, Agent, or Firm* — Roche Diagnostics Operations, Inc.

(57) ABSTRACT

The present disclosure relates to a luminescence method of detecting an analyte in a liquid sample comprising marking the analyte with a marker capable of effecting luminescence upon application of excitation energy, wherein reference data descriptive of the luminescence decay is stored in an electronic memory; applying the excitation energy for causing the luminescence; time-resolved measuring of the luminescence over a period of time for acquisition of a measurement signal; reading the reference data from the electronic memory; comparing the measurement signal with the luminescence decay described by the reference data; generating an output signal indicative of the presence of the analyte in the liquid sample using the measurement signal; in case of a mismatch of the measurement signal and the luminescence decay described by the reference data, generating an error signal.

6 Claims, 11 Drawing Sheets

LUMINESCENCE METHOD OF DETECTING AN ANALYTE IN A LIQUID SAMPLE AND ANALYSIS SYSTEM

FIELD OF THE DISCLOSURE

The present disclosure relates to the detection of an analyte in a liquid sample by effecting luminescence, such as by using a luminescence immunoassay, and a respective analysis system.

BACKGROUND

Numerous methods and systems have been developed for the detection and quantitation of analytes of interest in biochemical and biological substances. Methods and systems which are capable of measuring trace amounts of microorganisms, pharmaceuticals, hormones, viruses, antibodies, nucleic acids and other proteins are of great value to researchers and clinicians.

A body of art has been developed based upon the well known binding reactions, e.g., antigen-antibody reactions, nucleic acid hybridization techniques, and protein-ligand systems. The high degree of specificity in many biochemical and biological binding systems has led to many assay methods and systems of value in research and diagnostics. Typically, the existence of an analyte of interest is indicated by the presence or absence of an observable "label" attached to one or more of the binding materials.

Chemiluminescent assay techniques where a sample containing an analyte of interest is mixed with a reactant labeled with a chemiluminescent label have been developed. The reactive mixture is incubated and some portion of the labeled reactant binds to the analyte. After incubation, the concentration of the label in either or both fractions can be determined by chemiluminescent techniques. The level of chemiluminescence determined in one or both fractions indicates the amount of analyte of interest in the biological sample.

Electrochemiluminescent (ECL) assay techniques are an improvement on chemiluminescent techniques. They provide a sensitive and precise measurement of the presence and concentration of an analyte of interest. In such techniques, the incubated sample is exposed to a potentiostatically or galvanostatically controlled working electrode in order to trigger luminescence. In the proper chemical environment, such electrochemiluminescence is triggered by a voltage or current impressed on the working electrode at a particular time and in a particular manner. The light produced by the label is measured and indicates the presence or quantity of the analyte. For a fuller description of such ECL techniques, reference is made to, e.g., U.S. Pat. No. 5,238,808 and Int. Pat. Appln. Pub. No. WO 86/02734.

U.S. Pat. No. 6,881,536 B1 shows a specific binding assay method based on a luminescent phenomenon wherein inert microparticulate matter is specifically bound to one of the binding reactants of the assay system.

U.S. Pat. No. 6,599,473 B1 discloses an electrochemiluminescence binding reaction analysis (ECL-BBA).

In accordance with ECL-BBA a detectable complex is produced, whose concentration constitutes a measure of the analytic result sought. A marking substances (label) capable of effecting an ECL-reaction is coupled to a binding reagent specific for the analyte, e.g., an antibody. The species comprising the marking substance and the binding reagent is designated as a label conjugate.

When such a substance is subjected to a suitable electrical potential on a voltammetric working electrode, it emits light which can be measured photometrically. A second electrochemically active substance, designated as a co-reactand, normally contributes to this reaction. In practice, primarily a ruthenium complex (ruthenium-tris [bipyridyl]) is used as ECL-label in combination with TPA (tripropylamine) as co-reactand. The two electrochemically active substances are both oxidized upon voltage application to the electrode. Subsequent loss of a proton will turn the TPA into a strongly reducing species. The subsequent redox reaction brings the ECL-label into an excited state from which it returns to the ground state with the emission of a photon. The ECL-label reaction is typically a circular reaction so that a single label molecule emits a plurality of photons after application of a voltage to the electrode.

The ECL-marked complex molecules characteristic for the analysis are fixed to magnetic microparticles (beads). In practice, magnetized polystyrene beads having a diameter of typically 2 to 3 micrometers are used. Fixing is effected by means of a pair of specific biochemical binding partners. The pair streptavidin biotin has turned out to be particularly advantageous. The beads are streptavidine-coated, to which a biotinylated antibody will bind.

The beads with the bound marked complex are introduced into the measuring cell of a measuring apparatus. The cell is equipped with electrodes which are necessary for generating the electrical field required for triggering the ECL-reaction. The beads are drawn onto the surface of the working electrode in the magnetic field of a magnet disposed below the working electrode. Since this typically occurs in flow-through cells with continuously flowing sample fluids, the magnetic deposition of the beads is designated as "capturing". An electric potential required for triggering the ECL-reaction is then applied to the working electrode and the resulting luminescence light is measured using a suitable optical detector. The intensity of the luminescence light is a measure for the concentration of the number of labeled antibodies coupled to the beads on the surface of the working electrode which, in turn, is a measure of the concentration of the analyte in the sample. A calibration allows calculation of the sought concentration from the measured luminescence signal.

A plurality of different variations of this type of ECL-BBA-method have been discussed and described in the literature.

SUMMARY

It is against the above background that the embodiments of the present disclosure provide certain unobvious advantages and advancements over the prior art. In particular, the applicant has recognized a need for improvements in luminescence methods of detecting an analyte in a liquid sample and analysis systems.

In accordance with embodiments of the disclosure an analyte is detected in a liquid sample by marking the analyte with a marker capable of effecting luminescence upon application of excitation energy, wherein reference data being descriptive of the luminescence decay of the luminescence to be effected by the marker is stored in an electronic memory, applying the excitation energy for causing the luminescence, timeresolved measuring of the luminescence over a period of time for acquisition of a measurement signal, reading the reference data from the electronic memory, comparing the measurement signal with the luminescence decay described by the reference data, generating an output signal being indicative of the presence of the analyte in the liquid sample using the measurement signal, and in case of a mismatch of the measurement signal and the luminescence decay described by the reference data, generating an error signal.

An "analyte" as understood herein is a component of the liquid sample to be analyzed, e.g., molecules of various sizes, proteins, metabolites and the like.

A "liquid sample" as understood herein encompasses a biological sample such as any kind of tissue or body fluid having been derived from a human or any other organism. In particular, a biological sample can be a blood-, serum-, plasma-, urine-, cerebral-spinal fluid-, or saliva-sample or any derivatives thereof.

The term "luminescence" as understood herein encompasses any kind of luminescence such as radiation-induced luminescence, chemiluminescence and electrochemiluminescence, in particular ECL-BBA.

The term "luminescence immunoassay" as understood herein encompasses any immunoassay that produces an optical signal, i.e., a luminescence signal, that indicates the presence of a particular analyte in a liquid sample.

The point of departure of the present disclosure is the surprising discovery that the application of excitation energy for causing the luminescence may also cause an interfering signal in rare instances. Surprisingly, such an interfering signal has a decay characteristic that differs from the decay of the specific luminescence signal originating from the marker. The interfering signal may be superimposed on the luminescence signal produced by the luminescence immunoassay and may thus lead to a faulty measurement result.

Although the embodiments of the present disclosure are not limited to specific advantages or functionality, it is noted that this discovery is utilized in accordance with the present disclosure for identifying the presence of an interfering signal in the measurement signal. If the presence of the interfering signal is detected, an error signal may be generated in order to inform a user that the output signal which is provided on the basis of the measurement signal may be erroneous and may indicate the presence of an analyte which is in fact not present in the liquid sample or a wrong concentration of the analyte in the liquid sample.

In accordance with embodiments of the disclosure, unwanted interfering signal that is unintentionally caused by the application of excitation energy and which would otherwise lead to a faulty measurement result can be identified. For example, the interfering signal component is caused by some physical and/or chemical property of the substances that are present in the measurement cell.

It has been found that the occurrence of such an interfering signal is extremely rare. Nevertheless, the secure identification of a faulty measurement signal that results from the superposition of an interfering signal is crucial to avoid a misdiagnosis in such extremely rare cases. Such unwanted interference signals may be caused by the presence of autoluminescent substances within the measurement cell.

For example, in rare cases autoluminescent molecules may be contained in a patient's liquid sample in a concentration that is high enough to cause the interfering signal with a substantial signal strength upon application of the excitation energy thus leading to a faulty measurement signal. Such a concentration of autoluminescent molecules may be caused by some special condition, rare disease or pathology of the patient.

In accordance with embodiments of the disclosure the reference data that describes the luminescence decay of the luminescence signal caused by the marker is descriptive of a linear law relating to the maximum amplitude of the luminescence signal to a luminescence level of the luminescence signal reached after a given decay time. This is based on the surprising discovery of a linear relationship of the maximum amplitude of the luminescence signal and the remaining luminescence level reached after a predefined decay time. If an interfering signal is caused by the application of the excitation energy, the interfering signal superimposes on the luminescence signal such that the resulting measurement signal has a decay time that does not fulfill this linear law. This enables to detect the presence of the interfering signal in the measurement signal.

In accordance with embodiments of the disclosure a reference dataset is stored for a plurality of analytes and luminescence immunoassays. Each reference dataset is descriptive of a linear law relating the maximum amplitude of the luminescence to a luminescence level reached after a decay time which is specific for an immunoassay that is used for detecting the analyte. This is based on the surprising discovery that such a linear law exists irrespective of the specific immunoassay that is utilized for the detection of the analyte and that this linear law is specific for a given luminescence immunoassay. In other words, the relation between the maximum amplitude and the remaining signal level after a given decay time is always linear, but the ordinate and slope of the linear law is specific for the luminescence immunoassay.

Embodiments of the disclosure may be applicable to various kinds of luminescence techniques, including chemiluminescence and electrochemiluminescence, in particular ECL-BBA.

In accordance with another embodiment, the present disclosure relates to an analysis system for detecting an analyte in a liquid sample.

Embodiments of the analysis system comprise an incubator for receiving a liquid comprising the analyte and a marker for marking the analyte, the marker being capable of effecting luminescence upon application of excitation energy, an electronic memory storing reference data being descriptive of the luminescence decay of the luminescence to be effected by the marker, a trigger component for applying the excitation energy for causing the luminescence, an acquisition component for time-resolved measuring of the luminescence over a period of time, the acquisition component being operable to provide measurement signal, a data processing component being operable to read the reference data from the electronic memory, compare the measurement signal with the luminescence decay described by the reference data, generate an output signal being indicative of the presence of the analyte in the liquid sample using the measurement signal, in case of a mismatch of the measurement signal and the luminescence decay described by the reference data, generating an error signal.

In accordance with embodiments of the disclosure the incubation time can be shortened and the throughput of the analysis system can thus be improved. This is due to the fact that the incubation does not need to be performed until an equilibrium state is reached. In contrast, a relatively short incubation time can be sufficient for formation of a relatively small number of sandwiches that contribute to the luminescence signal. This is because the luminescence signal produced by the sandwiches can be relatively weak in comparison to the interference signal as embodiments of the disclosure enable to securely detect the presence of an interference signal in the measurement signal even if the luminescence signal is relatively weak.

In accordance with embodiments of the disclosure a luminescence immunoassay of the sandwich or the competitive type is utilized.

These and other features and advantages of the embodiments of the present disclosure will be more fully understood from the following detailed description taken together with the accompanying claims. It is noted that the scope of the claims is defined by the recitations therein and not by the specific discussion of features and advantages set forth in the present description.

BRIEF DESCRIPTION OF THE DRAWINGS

The following detailed description of the embodiments of the present disclosure can be best understood when read in conjunction with the following drawings, where like structure is indicated with like reference numerals and in which.

Skilled artisans appreciate that elements in the figures are illustrated for simplicity and clarity and have not been drawn to scale. For example, the dimensions of some of the elements in the figures may be exaggerated relative to other elements to help improve understanding of the embodiments of the present disclosure.

DETAILED DESCRIPTION

Figure 1:
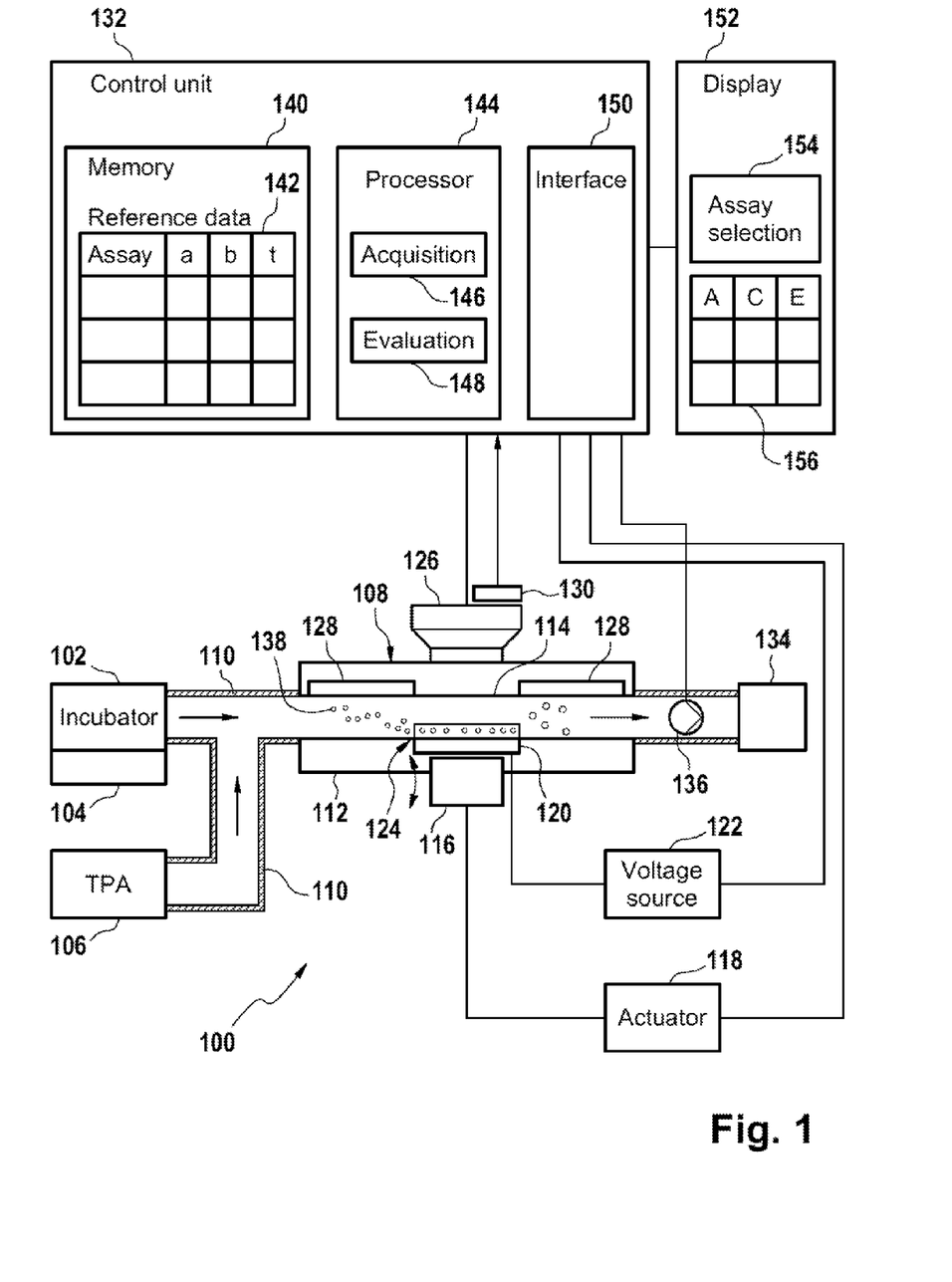
FIG. 1 is a block diagram of an analysis system in accordance with one embodiment of the present disclosure.

FIG. 1 shows an analysis system 100 for detecting an analyte in a liquid sample. The analysis system 100 comprises an incubator 102 for receiving a liquid 104 that is a mixture of an aliquot of the liquid sample and a marker for marking the analyte, such as of a luminescence immunoassay.

The analysis system 100 comprises a reservoir 106 that contains the co-reactant of the electrochemical reaction causing the luminescence. The incubator 102 and the reservoir 106 are coupled to a measurement cell 108 of the analysis system 100 by a pipe system 110 through which a portion of the liquid 104 and the co-reactant can flow into the measurement cell 108.

The measurement cell 108 comprises a cell body 112 that has a conduit 114 for receiving a portion of the liquid 104 and of the co-reactant through the pipe system 110. The measurement cell 108 has a magnetic component 116, such as a permanent magnet, for providing a magnetic field in the measurement cell 108. The magnetic component 116 may be coupled to an actuator 118 for rotating the magnetic component 116 to and from the conduit 114 in order to switch on or off the magnetic field within the conduit 114.

The magnetic component 116 is positioned below a working electrode 120 that is coupled to a voltage source 122. An excitation area 124 is formed in the conduit 114 within the magnetic field caused by the magnetic component 116 on the working electrode 120.

Luminescence that is caused in the excitation area 124 by the application of excitation energy, i.e., the application of a voltaic trigger pulse on the working electrode 120, is measured by means of an optical sensor, such as a photomultiplier 126. The optical sensor is sensitive within a certain frequency range such that it provides a measurement signal to which an interfering signal may contribute, such as a luminescence signal caused by autoluminescent molecules that may be present in the measurement cell 108, provided that the luminescence is within the sensor's frequency range.

The photomultiplier 126 is positioned opposite to the excitation area 124 over a window formed by counter electrodes 128 of the working electrode 120 through which the luminescence photons and any interfering photons caused by the excitation energy impinge on the photomultiplier 126. A resultant time resolved measurement signal 130 is provided from the photomultiplier 126 to a control unit 132 of the analysis system 100.

After a measurement has been performed the liquid contained within the conduit 114 is removed into a liquid waste container 134 and the measurement cell 108 is regenerated for a subsequent acquisition of a measurement signal 130.

The control unit 132 is coupled to the voltage source 122 in order to control the voltage source 122 to apply the trigger signal to the working electrode 120. The control unit 132 is also coupled to the actuator 118 for controlling the actuator 118 to switch on and off the magnetic field by moving the magnetic component 116, e.g., permanent magnet, correspondingly.

Further, the control unit 132 may be coupled to a "sipper unit", i.e., a pump 136, for extracting a portion of the liquid 104 from the incubator 102 and a portion of the coreactant from the reservoir 106 as well as for removing the liquid from the measurement cell 108 and regeneration of the measurement cell. In addition, the control unit 132 may be coupled to additional robotic components such as a pipetting station 174 (cf., embodiment of FIG. 3).

The measurement cell 108 may be adapted for performing ECL-BBA using various luminescence immunoassays.

For example, the liquid 104 may contain a mixture of an aliquot of the liquid sample, streptavidin coated magnetic particles, biotinylated antibodies and ruthenylated antibodies to form a so-called "sandwich" whereas the co-reactant contained in the reservoir 106 is tripropylamine (TPA). Hence, magnetic particles 138 with a bound label flow into the conduit 114. The magnetic particles 138 are immobilized on the working electrode 120 when the magnetic field is switched on. Next, the trigger pulse is applied on the working electrode 120 to cause the electrochemiluminescence in accordance with the ECL-BBA technique.

The control unit 132 has an electronic memory 140 for storing reference data 142 that describes the luminescence decay of a valid measurement signal 130 without a superimposed interfering signal. That reference data is specific for the luminescence immunoassay that is utilized for the detection of the analyte.

In the embodiment considered here the reference data 142 is stored in a lookup table or database table. The reference data 142 can comprise a reference dataset for each luminescence immunoassay supported by the analysis system 100. For example, for each supported immunoassay two coefficients a and b as well as a time t is stored in the memory 140. The coefficients a and b describe a linear law relating the maximum amplitude of the luminescence signal to a luminescence level reached after the decay time t. Storing the decay time t as part of the reference data may be superfluous if the considered decay time t is always the same.

The control unit 132 has at least one electronic processor 144 for execution of program modules, i.e., acquisition module 146 and evaluation module 148. Acquisition program module 146 is executed by the processor 144 for acquisition of the measurement signal 130 whereas the evaluation program module 148 is executed by the processor 144 for evaluation of the acquired measurement signal 130.

The control unit 132 has an interface 150 for coupling a display 152 or another human-machine-interface to the control unit 132. The display 152 may be implemented as a graphical user interface for displaying an input, such as an assay selection window 154 for a user's selection of one of the luminescence immunoassays supported by the analysis system 100 as well as an output, such as an analysis result window 156 for displaying a result of the analysis.

The result of the analysis performed by the analysis system 100 may be output as tabular data as depicted in FIG. 1 wherein the column A indicates the analyte to be detected and the column C indicates the concentration of the analyte that has been detected. The column E serves to indicate whether the detected concentration may be erroneous such as by displaying a flag or other warning signal or symbol, such as a red question—or exclamation mark.

In operation a user selects one of the luminescence immunoassays supported by the analysis system 100 by entering a respective selection into the assay selection window 154. The analysis of the liquid sample is started by execution of the acquisition program module 146 such that the pump 136 is controlled to transport a portion of the liquid 104 and of the co-reactant into the conduit 114.

Next, the actuator 118 is controlled to flip the magnetic component 116, e.g., permanent magnet, into a position such that its magnetic field is applied to the conduit 114 for immobilization of the magnetic particles 138 with their bound labels on the working electrode 120. Next, the voltage source 122 is controlled to apply the trigger pulse onto the working electrode 120 for excitation of the luminescence such that the measurement signal 130 results.

The measurement signal 130 is acquired by sampling the output of the photomultiplier 126 over a given period of time, such as 2 seconds after application of the trigger pulse by the voltage source 122, for time-resolved measuring of the luminescence.

The data samples that constitute the measurement signal 130 are stored within the memory 140 of the control unit 132 and the evaluation program module 148 is started for evaluation of the acquired measurement signal 130. By execution of the evaluation program module 148 the amplitude of the measurement signal 130 is determined. Next, the evaluation program module 148 performs a read access to the reference data 142 by reading the coefficients a and b of the user-selected immunoassay as well as the time t.

By means of the linear law described by a and b the expected signal level reached by the measurement signal 130 after time t is calculated and compared to the actual signal level of the measurement signal 130 after that time t. In case of a mismatch, i.e., if the actual signal level of the measurement signal 130 is a predefined margin below or above the expected signal level, a mismatch and thus the presence of a superimposed interfering signal is detected.

Next, the concentration C of the analyte, if any, in the liquid is determined by the evaluation program module 148 by means of the measurement signal 130 and the determined concentration C is flagged by an error signal E if the mismatch has been detected.

Next, the pump 136 is controlled by the control unit 132 for removing the liquid from the conduit 114 and regeneration of the measurement cell 108.

Figure 2:
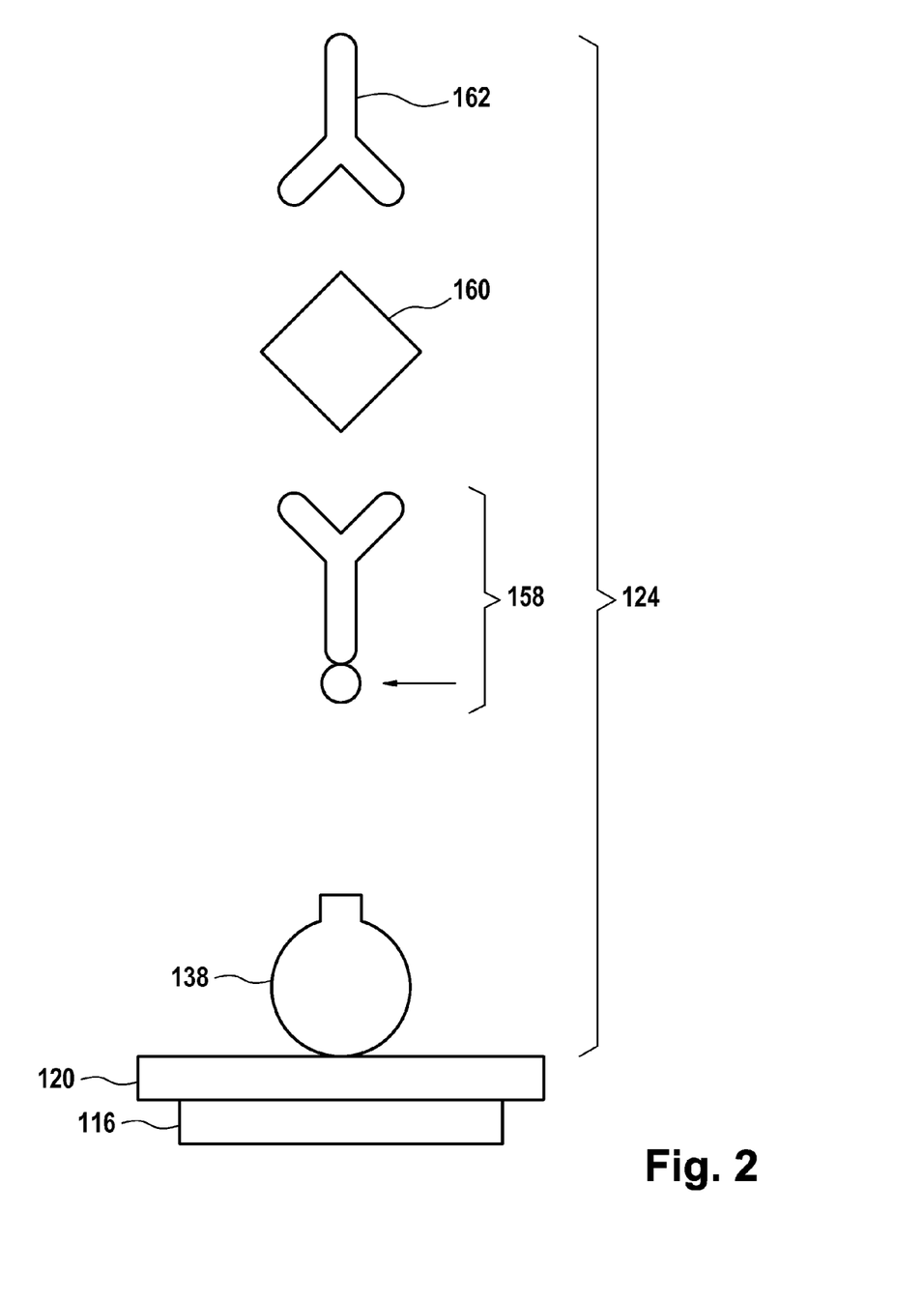
FIG. 2 is a diagram illustrating the ECL-BBA technique in accordance with one embodiment of the present disclosure.

FIG. 2 is illustrative of the "sandwich" that is formed within the incubator 102 and to which a trigger pulse is applied within the excitation area 124 on the working electrode 120. In the embodiment considered here each of the magnetic particles 138 can have a diameter of about 2.8 micrometers. The magnetic particle 138 is bound to a biotinylated antibody 158 of the immunoassay that is chosen depending on the analyte 160 to be detected. A ruthenium complex (ruthenium-tris [bipyridyl]) bound to an antibody 162 that is chosen depending on the analyte 160 is utilized as a luminescent label in the embodiment considered here.

Upon application of the voltaic trigger pulse an electrochemical reaction is induced with the tripropylamine in accordance with the ECL-BBA technique such that luminescence is caused.

Figure 3:
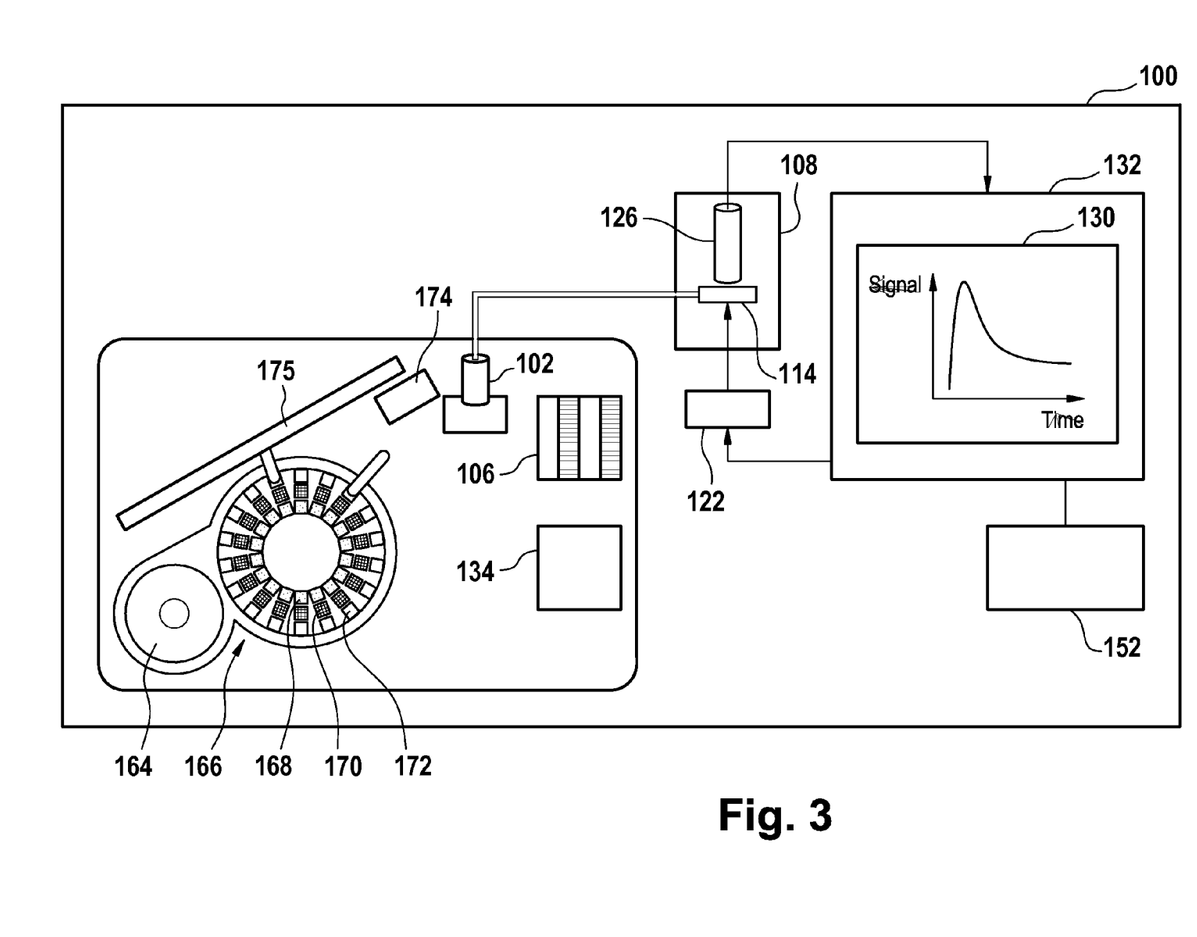
FIG. 3 is a block diagram of a further embodiment of an analysis system comprising a robotic component.

FIG. 3 shows a further embodiment of an analysis system 100. The analysis system 100 has a first rotor 164 for receiving receptacles, such as sample tubes, where each sample tube contains a liquid sample. The first rotor 164 may hold a number of sample tubes for providing random access to a pipettor 175.

The analysis system 100 has a second rotor 166 for receiving first receptacles 168 containing streptavidin-coated magnetic microparticles, second receptacles 170 containing biotinylated antibodies and third receptacles 172 containing ruthenylated antibodies. The second rotor 166 may be implemented as a reagent disk as shown in FIG. 3 for providing access of the pipettor 175 to the various reagents contained in the receptacles 168, 170 and 172.

The analysis system 100 has a robotic component for providing a mixture to the incubator 102. In the embodiment considered here the robotic component is controlled by the control unit 132 and comprises a pipetting station 174 having the pipettor 175.

In operation the control unit 132 controls the pipettor 175 to extract an aliquot of the liquid sample from one of the sample tubes that are held by the first rotor 164 and to extract portions of the streptavidin-coated magnetic particles, the biotinylated antibodies and the ruthenylated antibodies from the first, second and third receptacles 168, 170 and 172, respectively, in order to provide the mixture which is then put into the incubator 102 for incubation during a predetermined amount of time, such as about 9 to about 27 min.

The control unit 132 controls the "sipper", e.g., the pump 136 (cf., FIG. 1), such that the liquid mixture flows from the incubator 102 into the conduit 114 of the measurement cell 108 together with the co-reactant, i.e., tripropylamine. Next, the control unit 132 controls the actuator 118, (cf., FIG. 1) to switch on the magnetic field and then the voltage source 122 to apply the voltaic trigger pulse.

The resultant measurement signal 130 is acquired by the control unit 132 by sampling the output of the photomultiplier 126.

In case the error signal is generated by the evaluation program module 148 (cf., FIG. 1) a rerun is performed in order to attempt a correct acquisition of the measurement signal 130 without a superimposed interfering signal. This is performed by cleaning and regenerating the measurement cell 108 followed by a repeated performance of the entire sequence starting with the extraction of another aliquot from the liquid sample to be analyzed.

Figure 4:
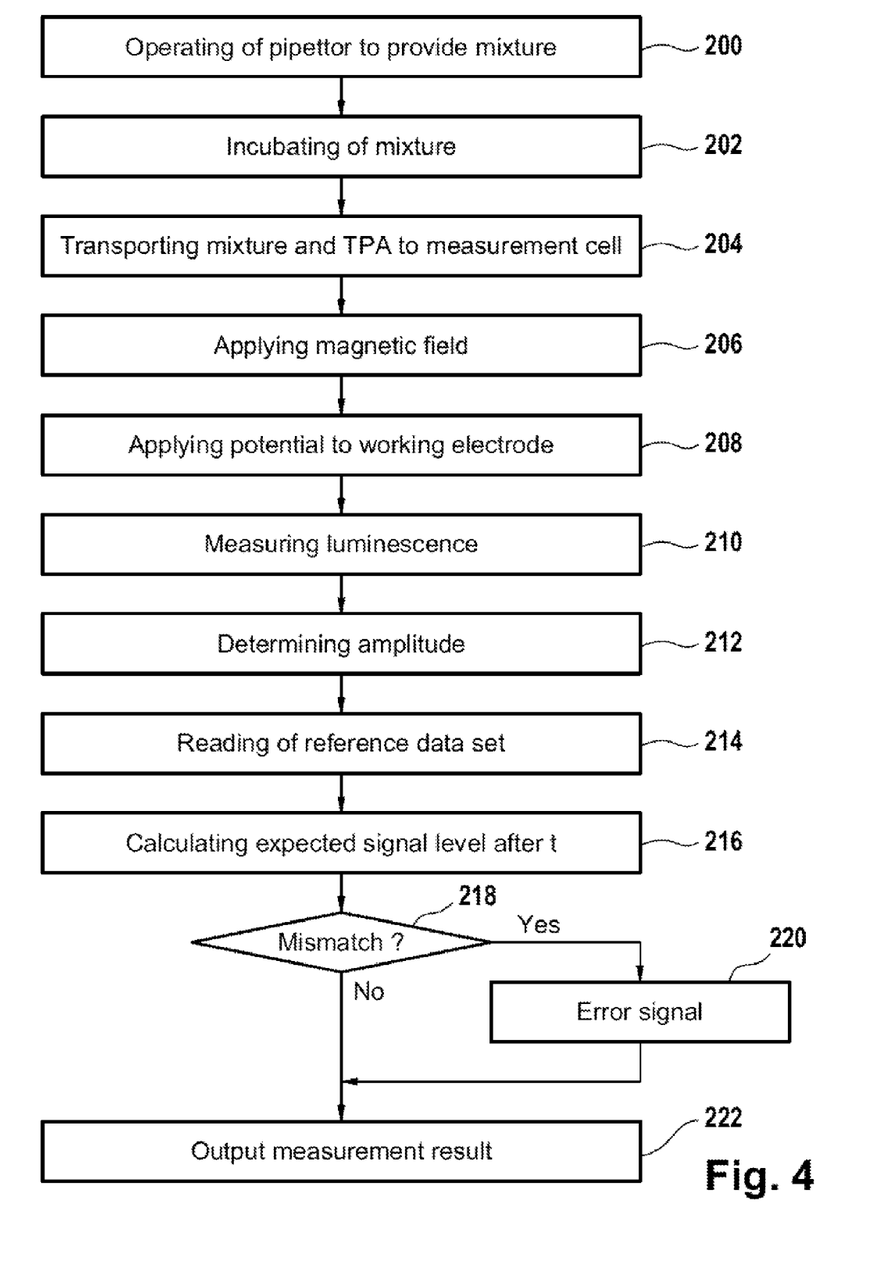
FIG. 4 is a flowchart illustrating a method in accordance with one embodiment of the present disclosure.

FIG. 4 shows a respective flowchart. In step 200 the pipettor of the analysis system is operated to provide the mixture of an aliquot of the liquid sample to be analyzed, the streptavidin-coated magnetic microparticles, the biotinylated antibodies and the ruthenylated antibodies. This mixture is incubated for a predefined time period in step 202 before it is transported together with tripropylamine (TPA) to the measurement cell in step 204.

In step 206 the magnetic field is switched on such that the bound magnetic microparticles are attracted towards the working electrode into the excitation area 124 (cf., FIG. 1). In step 208 an electrical potential is applied to the working electrode for providing a trigger pulse that causes the luminescence. In step 210 the resultant luminescence is measured over a given time period such as by sampling the output signal provided by the photomultiplier. In rare cases an interfering signal is also caused by the trigger pulse. In such a rare case the measurement signal results from the superimposition of the luminescence signal and the interfering signal.

In step 212 the maximum amplitude, i.e., the maximum signal level, of the acquired measurement signal is determined and in step 214 a reference dataset is read from the electronic memory of the analysis system. The reference dataset specifies a linear law that relates a measured maximum amplitude to a remaining signal level expected after a predefined decay time t.

In step 216 the expected signal level after time t is calculated using the reference dataset and the measured amplitude of the measurement signal. In step 218 it is determined whether a mismatch between the expected signal level and the actual signal level of the measurement signal after time t exists. If this is the case, an error signal is generated in step 220 which is output together with the measurement result in step 222. If no mismatch occurs the control goes directly from step 218 to step 222. The measurement result, i.e., the presence and/or concentration of the analyte, is obtained from the measurement signal using appropriate calibration information, as it is as such known from the prior art.

Figure 5:
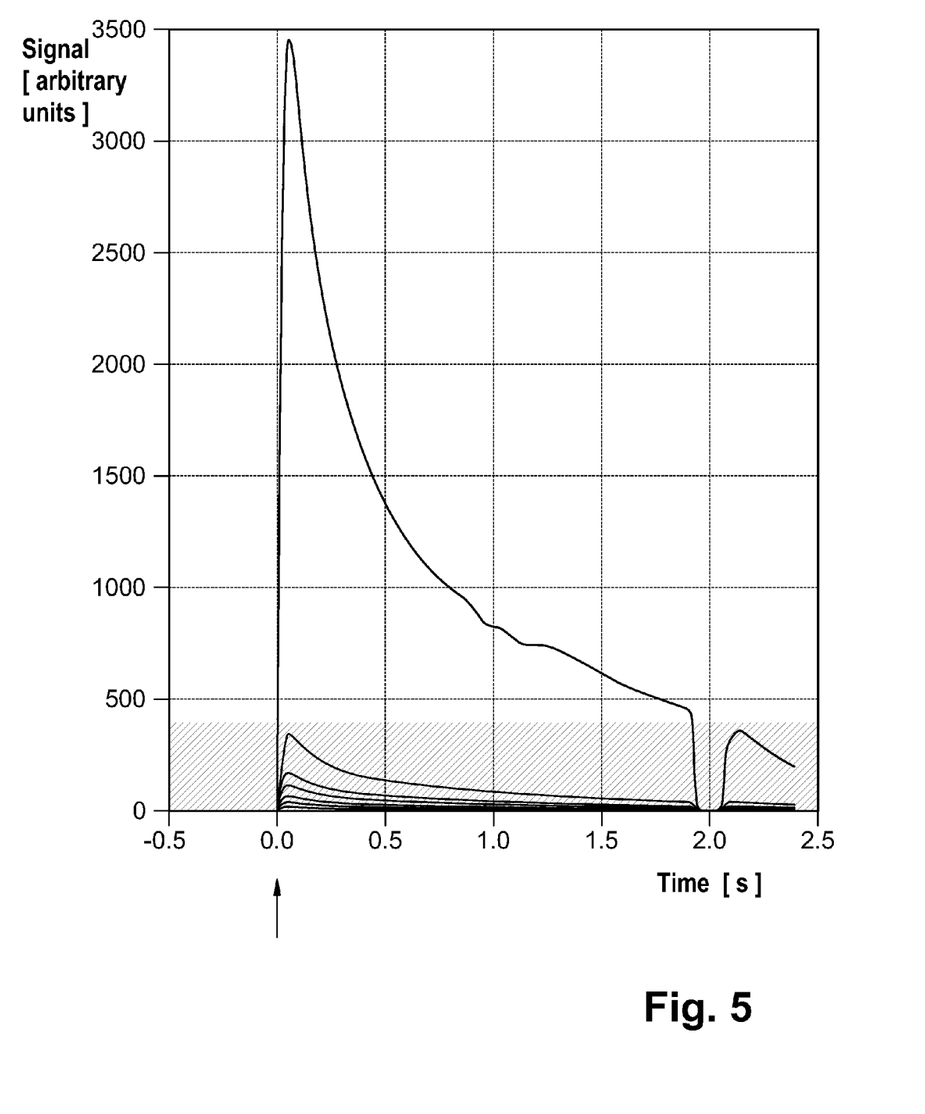
FIG. 5 is illustrative of the luminescence decay of a luminescence signal having various amplitudes.

FIG. 5 shows various measurement signals 130 that are acquired over a time interval of 2 seconds from the trigger pulse at t=0 seconds. The measurement signals shown in FIG. 5 are luminescence signals without having a superimposed interfering signal.

Figure 6:
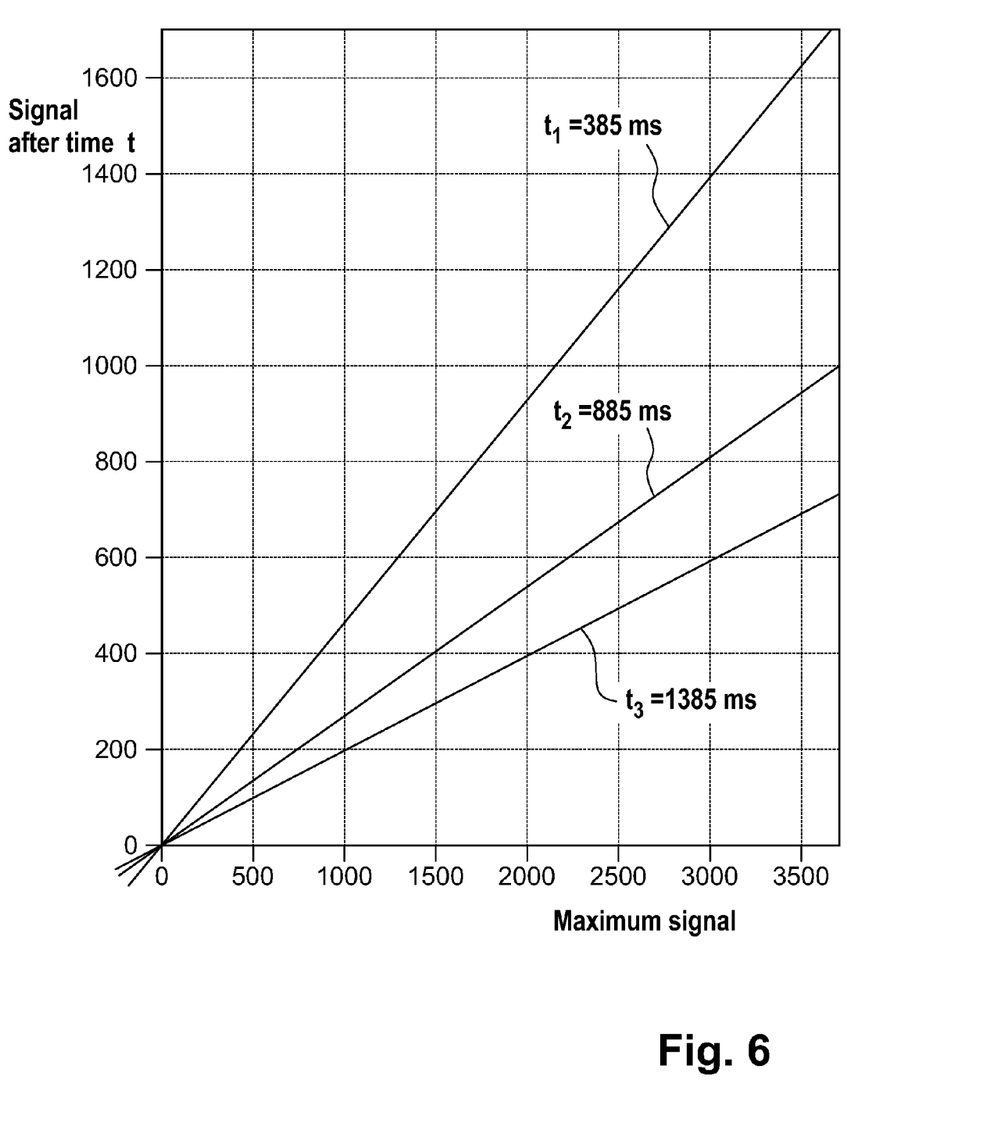
FIG. 6 is a diagram that illustrates the linear law relating the maximum amplitude of the luminescence signals depicted in FIG. 5 to a remaining luminescence signal level reached after a decay time t.

FIG. 6 shows a diagram that is obtained from the measurement signals depicted in FIG. 5 relating the amplitude ("maximum signal") of the measurement signals to the remaining signal level at the time t. As apparent from FIG. 6 there is a linear law that relates the amplitude of the luminescence signal to the remaining signal level after the time t where three exemplary curves are given in FIG. 6 for decay times $t_1$=385 milliseconds, $t_2$=885 milliseconds and $t_3$=1385 milliseconds.

Figure 7:
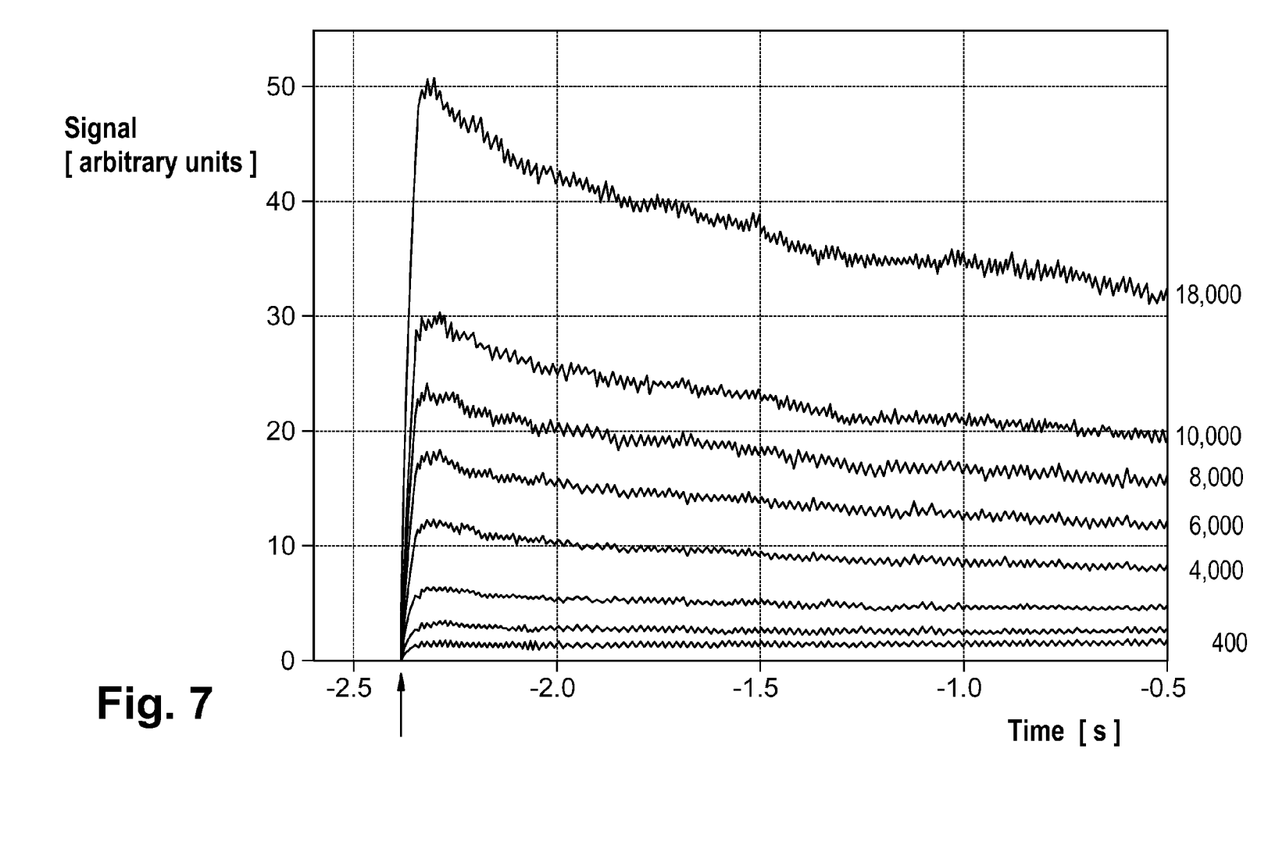
FIG. 7 is illustrative of the decay characteristics of an interfering signal without the presence of an analyte-specific luminescence signal for various amplitudes of the interfering signal.

FIG. 7 shows another set of measurement signals that have been acquired without the presence of a marker and thus without a luminescence signal. Hence, the measurement signals depicted in FIG. 7 are pure interfering signals that are not caused by a marker. FIG. 7 shows the signal level of each interfering signal starting with the trigger pulse over time. As shown in FIG. 7 the interfering signals that are caused by the trigger pulse have also a signal decay characteristic which is however different from that of the luminescence signals depicted in FIG. 5 as the signal decay is slower for the interfering signal.

Figure 8:
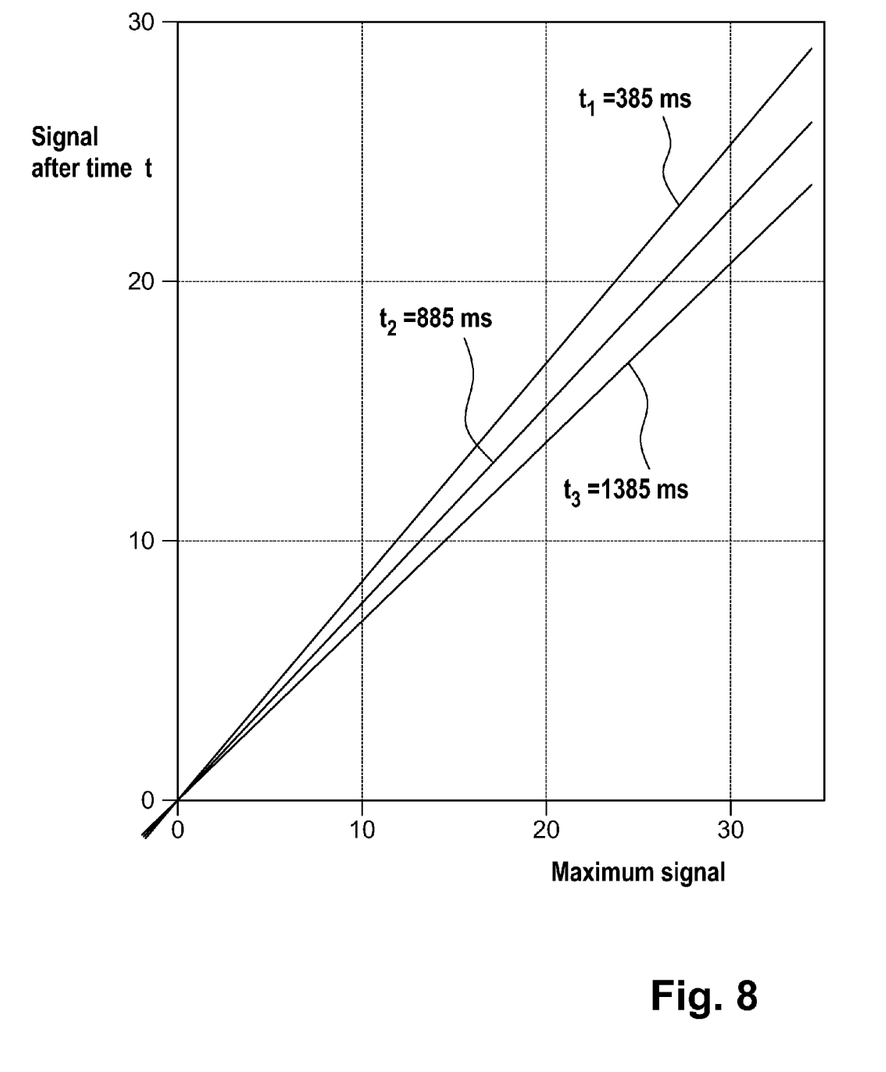
FIG. 8 is illustrative of the linear law relating the maximum amplitude of the interfering signal to a signal level reached after a decay time t.
Figure 9A:
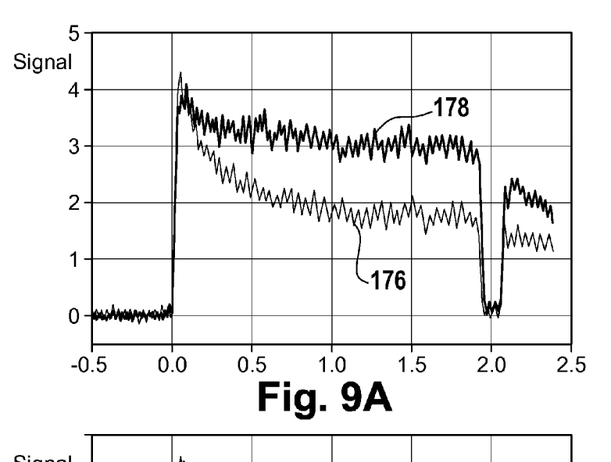
FIGS. 9a to 9d are illustrative of the decay characteristics of luminescence signals and interfering signals.
Figure 9B:
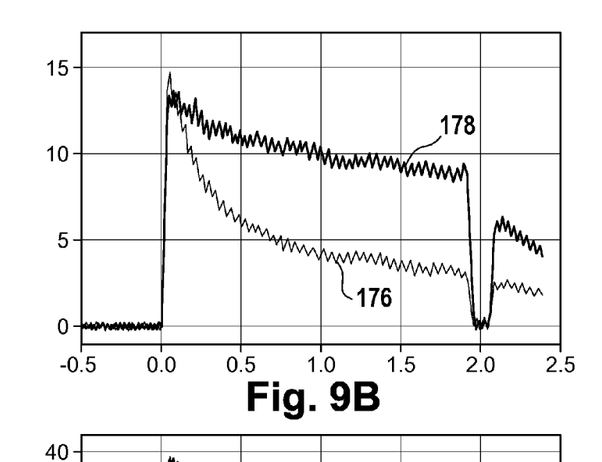
Figure 9C:
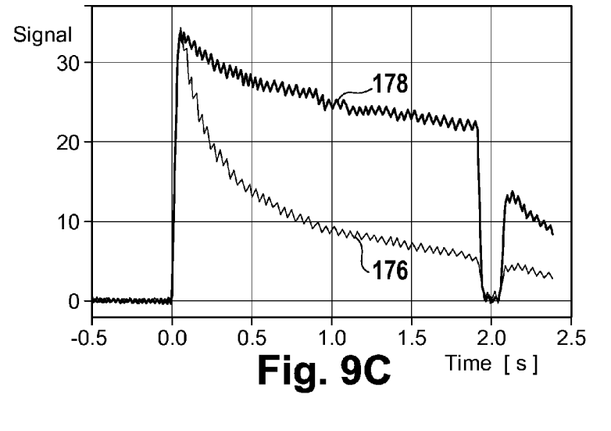
Figure 9D:
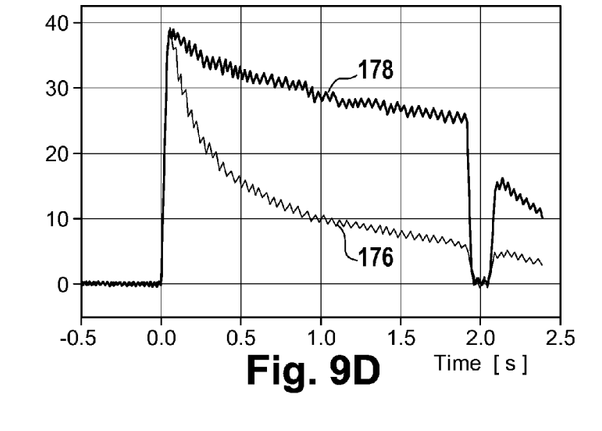

FIG. 8 is a diagram based on the data shown in FIG. 7 analogous to that of FIG. 6. As apparent from FIG. 8 the relationship between the amplitudes of the interfering signals with the remaining signal after a given time is also of a linear nature.

FIGS. 9a to 9d show diagrams illustrating the different luminescence decay characteristics over time of a luminescence signal 176 that originates from the marker and of an interfering signal 178 that is also caused by the excitation energy, e.g., the voltaic trigger pulse but is of another origin, such as an impurity. As apparent from FIGS. 9a to 9d the signal decay of the interfering signal 178 is slower in comparison to the luminescence signal 176 irrespective of the signal amplitudes at time t=0.

Figure 10A:
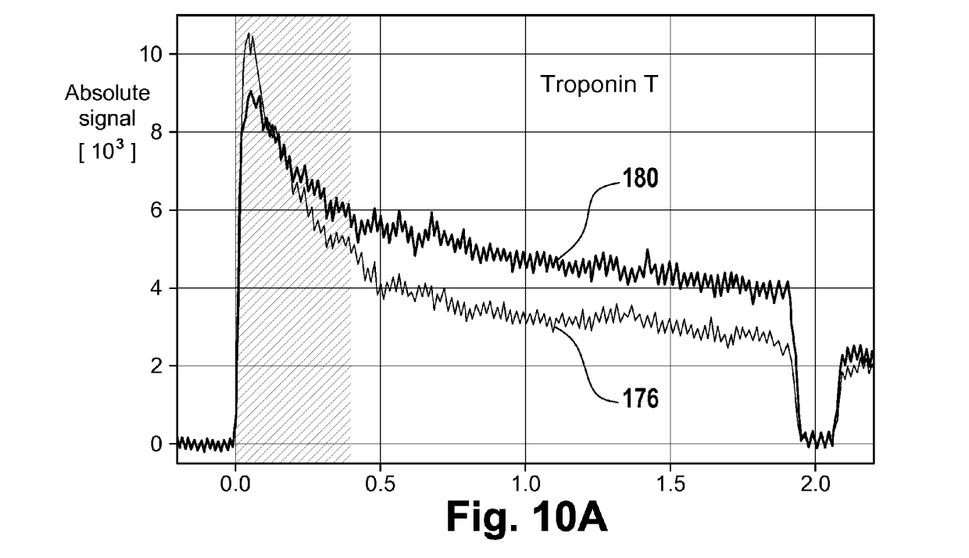
FIGS. 10a and 10b are illustrative of a luminescence signal without a superimposed interfering signal in comparison to a measurement signal that results from the superimposition of a luminescence signal and an interfering signal.
Figure 10B:
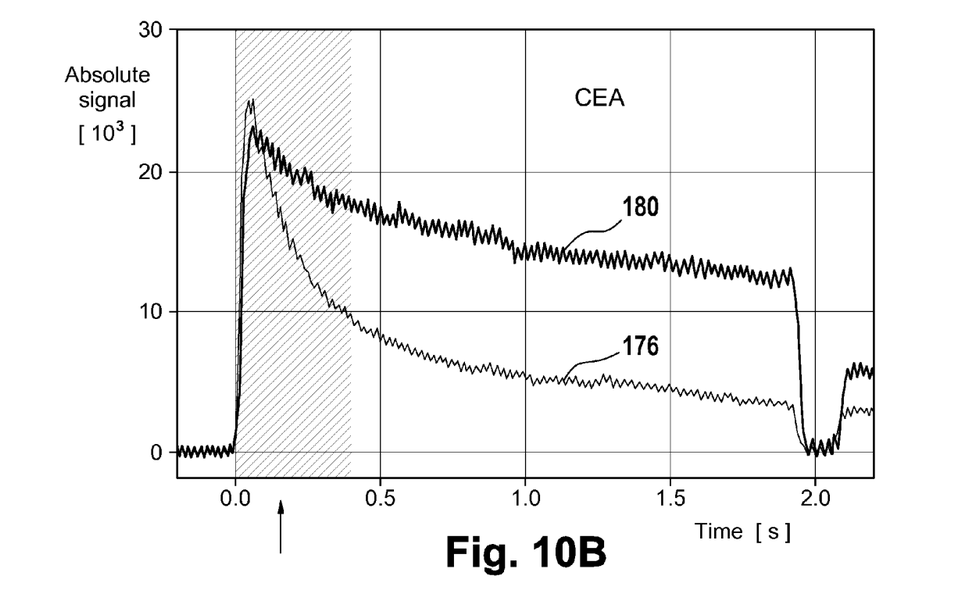

FIGS. 10a and 10b each show a luminescence signal 176 that has been measured using the immunoassays for detection of the analytes Troponin T and CEA, respectively.

The superposition signal 180 that is also depicted in FIGS. 10a and 10b has about the same amplitude as the luminescence signal 176 and consists of the superposition of a luminescence signal 176 with an interfering signal 178. As apparent from FIGS. 10a and 10b the superposition signal 180 has a slower decay characteristic in comparison to the luminescence signal 176 due to the superimposed interference signal 178.

The differing decay characteristics of the luminescence signal 176 and the superposition signal 180 enables to identify a faulty measurement that results from the excitation of not only the luminescence signal 176 but also an interfering signal 178. This enables to identify the superposition signal 180 to contain an error such that the respective measurement result may be disregarded and a rerun can be performed.

Figure 11A:
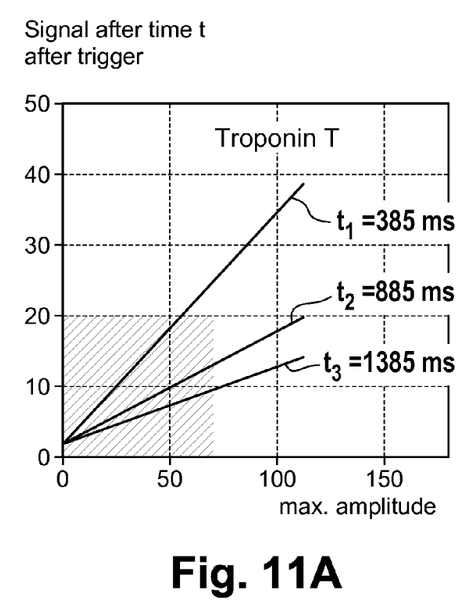
FIGS. 11a to 11c are illustrative of assay-specific linear laws relating the maximum amplitude of the luminescence signal to a luminescence signal level reached after a decay time t from the trigger signal.
Figure 11B:
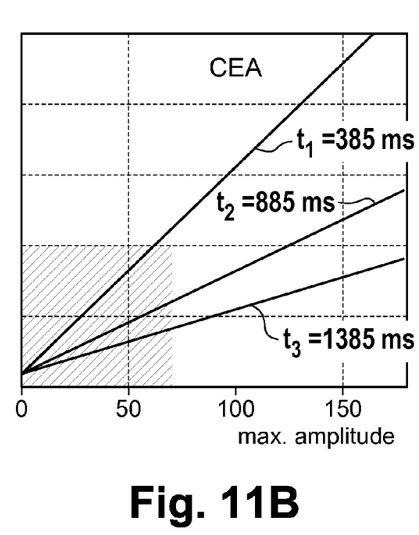
Figure 11C:
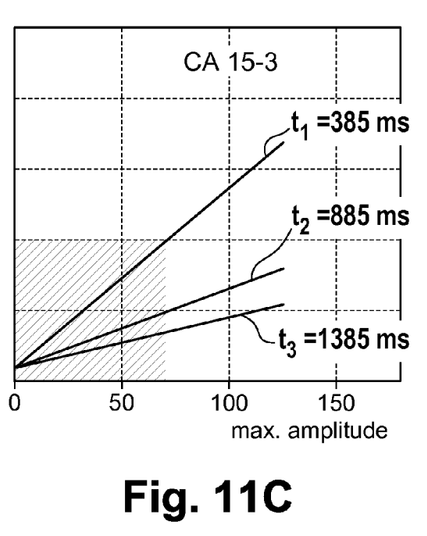

FIG. 11 a illustrates the linear relationship between the amplitude of a luminescence signal 176 at time t=0 when the excitation energy is applied and the remaining signal level after a decay time t for decay times $t_1$, $t_2$ and $t_3$. FIG. 11a shows this linear law for the immunoassay Troponin T whereas FIGS. 11b and 11c show this linear relationship for the immunoassays CEA and CA 15-3, respectively. As apparent from FIGS. 11a, 11b and 11c at least the slopes of the linear relations are assay-specific and the relationship as such is always of a linear nature.

|  | Troponin T | | | CEA | | |
| --- | --- | --- | --- | --- | --- | --- |
| decay time t[ms] after trigger pulse | 385 = $t_1$ | 885 = $t_2$ | 1385 = $t_3$ | 385 = $t_1$ | 885 = $t_2$ | 1385 = $t_3$ |
| a | 1.27 | 1.63 | 1.96 | 1.42 | 1.53 | 2.03 |
| b | 0.33 | 0.16 | 0.10 | 0.29 | 0.14 | 0.08 |

The above table shows reference datasets of this linear law for the immunoassays troponin T and CEA. Each reference dataset comprises the coefficient a and b for the times $t_1$, $t_2$ and $t_3$ where a is the ordinate and b is the slope such that the remaining signal level y after a given decay time t is calculated as y=a+bx where x is the amplitude of the measured signal at time t=0, i.e., the time when the excitation energy is applied.

For determining a mismatch between the actual measurement signal and the luminescence decay described by the reference data the amplitude of the measurement signal is determined and the expected remaining signal level such as at time $t_1$ is calculated which yields the expected remaining signal level y at that time $t_1$. If the actual remaining signal level of the measurement signal differs more than a predefined margin from the expected signal level a mismatch and thus the presence of an interfering signal 178 is identified.

It is noted that terms like "preferably", "commonly", and "typically" are not utilized herein to limit the scope of the claimed subject matter or to imply that certain features are critical, essential, or even important to the structure or function of the embodiments disclosed herein. Rather, these terms are merely intended to highlight alternative or additional features that may or may not be utilized in a particular embodiment of the present disclosure.

It is also noted that the terms "substantially" and "about" may be utilized herein to represent the inherent degree of uncertainty that may be attributed to any quantitative comparison, value, measurement, or other representation. These terms are also utilized herein to represent the degree by which a quantitative representation may vary from a stated reference without resulting in a change in the basic function of the subject matter at issue.

It will be apparent to those skilled in the art that various equivalents, changes, and modifications may be made to the embodiments described herein without departing from the spirit and scope of the claimed subject matter. Thus it is intended that the specification cover the modifications and variations of the embodiments described herein provided such modifications and variations come within the scope of the appended claims and their equivalents.

What is claimed is:

1. An analysis system for detecting an analyte in a liquid sample comprising
    an incubator configured to receive a liquid comprising the analyte and a marker for marking the analyte, the marker being capable of effecting luminescence upon application of excitation energy,
    an electronic memory storing reference data being descriptive of the luminescence decay of the luminescence to be effected by the marker,
    a trigger component configured for applying the excitation energy for causing the luminescence,
    an acquisition component configured for time-resolved measuring of the luminescence over a period of time, the acquisition component being further configured to provide a measurement signal,
    an evaluation module configured to
        read the reference data from the electronic memory,
        compare the measurement signal with the luminescence decay described by the reference data,
        generate an output signal being indicative of the presence of the analyte in the liquid sample using the measurement signal, the evaluation module comprising,
            an interfering signal detector, the interfering signal detector configured to generate an error signal in case of a mismatch of the measurement signal and the luminescence decay described by the reference data,
        compare the measurement signal with the luminescence decay described by the reference data,
        determine the maximum amplitude from the measurement signal,
        use the reference data to calculate an expected level of the luminescence after the decay time using the maximum amplitude, and
        compare the expected level and the measurement signal at the decay time for determining whether the mismatch exists, and
    a display interface comprising a tabular date output, wherein the tabular date output comprises a column E to indicate possible erroneous analyte measurement output.

2. The analysis system of claim 1, the reference data comprising a reference data set for a plurality of analytes, each analyte having an assigned reference data set, and further comprising an interface for receiving a signal being indicative of one of the analytes to be detected in the liquid sample, the evaluation module being operable to select one of the reference data sets of the reference data that is assigned to the analyte indicated by the received signal and to use the selected reference data set to perform the comparison between the measurement signal and the luminescence decay described by the reference data set.

3. The analysis system of claim 2, each reference data set being descriptive of an assay-specific linear law being descriptive of the luminescence decay.

4. The analysis system of claim 2, each reference data set being descriptive of an expected signal level of the measurement signal at a given time interval after the application of the excitation energy as a function of the amplitude of the measurement signal.

5. The analysis system of claim 1 further comprising a first receptacle containing streptavidin coated magnetic microparticles, a second receptacle containing biotinylated antibodies, a third receptacle containing ruthenylated antibodies, a robotic component for providing a mixture comprising a portion of the liquid sample, the streptavidin coated magnetic microparticles, the biotinylated antibodies, and the ruthenylated antibody to the incubator such that a sandwich comprising the anayte, the streptavidin coated magnetic microparticles,the biotinylated antibodies and the ruthenylated antibodies is formed in the incubator, a transportation component for transportation of a portion of the mixture from the incubator to a measurement cell and for transportation of tripropylamine to the measurement cell, a magnetic component for providing a magnetic field in the measurement cell for magnetic adhesion of the magnetic microparticles, and a control component for controlling the robotic component, the transportation component, the magnetic component, the trigger component and the acquisition component, such that the mixture is incubated in the incubator for a predetermined amount of time without reaching an equilibrium state before the portion of the mixture is transported into the measurement cell for performing the time-resolved measurement.

6. The analysis system of claim 5, wherein the control component is configured to perform a rerun in response to the error signal, and wherein the robotic component is controlled to provide the mixture with another portion of the liquid sample for the rerun.

* * * * *